United States Patent [19]
Su

[11] Patent Number: 5,861,267
[45] Date of Patent: *Jan. 19, 1999

[54] METHODS, NUCLEOTIDE SEQUENCES AND HOST CELLS FOR ASSAYING EXOGENOUS AND ENDOGENOUS PROTEASE ACTIVITY

[75] Inventor: Michael Su, Newton, Mass.

[73] Assignee: Vertex Pharmaceuticals Incorporated, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 432,693

[22] Filed: May 1, 1995

[51] Int. Cl.$^6$ .............................. C12Q 1/37; C12N 1/14
[52] U.S. Cl. .................... 435/23; 435/6; 435/24; 435/212; 435/219; 435/375; 435/410; 435/254.11; 435/254.2; 435/320.1; 536/23.1; 536/23.2; 536/23.7; 536/23.72
[58] Field of Search .............................. 435/6, 212, 213, 435/214, 217, 218, 219–226, 23, 24, 325, 410, 254.11, 254.2, 320.1; 536/23.1, 23.2, 23.7, 23.72

[56] References Cited

U.S. PATENT DOCUMENTS 5,478,727  12/1995  Roizman et al. ..................... 435/23

FOREIGN PATENT DOCUMENTS

| 0 421 109 A3 | 4/1991 | European Pat. Off. . |
| WO 90/10075 | 9/1990 | WIPO . |
| WO 91/15575 | 10/1991 | WIPO . |
| WO 93/01305 | 1/1993 | WIPO . |
| WO 95/02059 | 1/1995 | WIPO . |
| WO 95/02065 | 1/1995 | WIPO . |

OTHER PUBLICATIONS

Failla, C., et al., "Both NS3 and NS4A Are Required for Proteolytic Processing of Hepatitis C Virus Nonstuctural Proteins", *Journal of Virology* 68, 3753–3760 (1994).

Grakoui, A. et al., "Characterization of the Hepatitis C Virus–Encoded Serine Proteinase: Determination of Proteinase–Dependent Polyprotein Cleavage Sites", *Journal of Virology* 67, 2832–2843 (1993).

F. Pecceu, et al. "Human Interleukin 1β Fused to the Human Growth Hormone Signal Peptide is N–Glycosylated ad Secreted by Chinese Hamster Ovary Cells", *Gene* 97, 253–258 (1991).

Sidors, W.M. et al., "Characterization of the Structural Requirements and Cell Type Specificity of IL–1α and IL–1β Secretion", *Journal of Biological Chemistry* 268, 22170–22174 (1993).

Giam et al. "In vivo and in vitr autoprocessing of human immunodeficiency virus protease expressed in *Escherichia coli*" J. Biol. Chem. 263, 14617–14620, Oct. 1988.

Babe et al. "Consititutive production of nonenvoloped human immunodeficincy virus type 1 particles by a mammalian cell line and effects of protease inhibitor on particle maturation" Antimicrobial Agents and Chemothearpy 38 (10), 2430–2439, Oct. 1994.

Pichuantest et al. "Recombinant HIV 1 protease secreted by Saccharomyces cervisiae correctly processes myristylated gag polyprotein" Proteins: Structure, Func. & Gen. 6, 324–337, 1989.

Pichuantest et al. "Recombinant HIV 2 protease processes HIV 1 Pr53 gag and analogous junction peptides in vitro" J. Biol. Chem. 265, 13890–13898, Aug. 1990.

Okano et al. "Functional expression of human leukocyte elastase (HLE)/medullasin in eukaryotic cells" Biochem. Biophys. Res. Comm. 167, 1326–1332, Mar. 1990.

Komoda et al. "Substrate requirements of hepatitis C virus serine protease for intermolecular polypeptide cleavage in *Escherichia coli*" J. Virol. 68, 7351–7357, Nov. 1994.

Creighton, T. E. "Proteins: Structure and Molecular Properties" Second Edition, 1993, W. H. Freeman and Company, New York, pp. 65–68, 1993.

*Primary Examiner*—Robert A. Wax
*Assistant Examiner*—Nashaat T. Nashed
*Attorney, Agent, or Firm*—James F. Haley, Jr.; Barbara A. Ruskin; Andrew S. Marks

[57] ABSTRACT

The invention relates to methods for assaying exogenous protease activity in a host cell transformed with nucleotide sequences encoding that protease and a specialized substrate. It also relates to methods for assaying endogenous protease activity in a host cell transformed with nucleotide sequences a specialized substrate. When these nucleotide sequences are expressed, the exogenous or endogenous protease cleaves the substrate and releases a polypeptide that is secreted out of the cell, where it can be easily quantitated using standard assays. The methods and transformed host cells of this invention are particularly useful for identifying inhibitors of the exogenous and endogenous proteases. If the protease is a protease from an infectious agent, inhibitors identified by these methods are potential pharmaceutical agents for the treatment or prevention of infection by that agent.

21 Claims, 7 Drawing Sheets

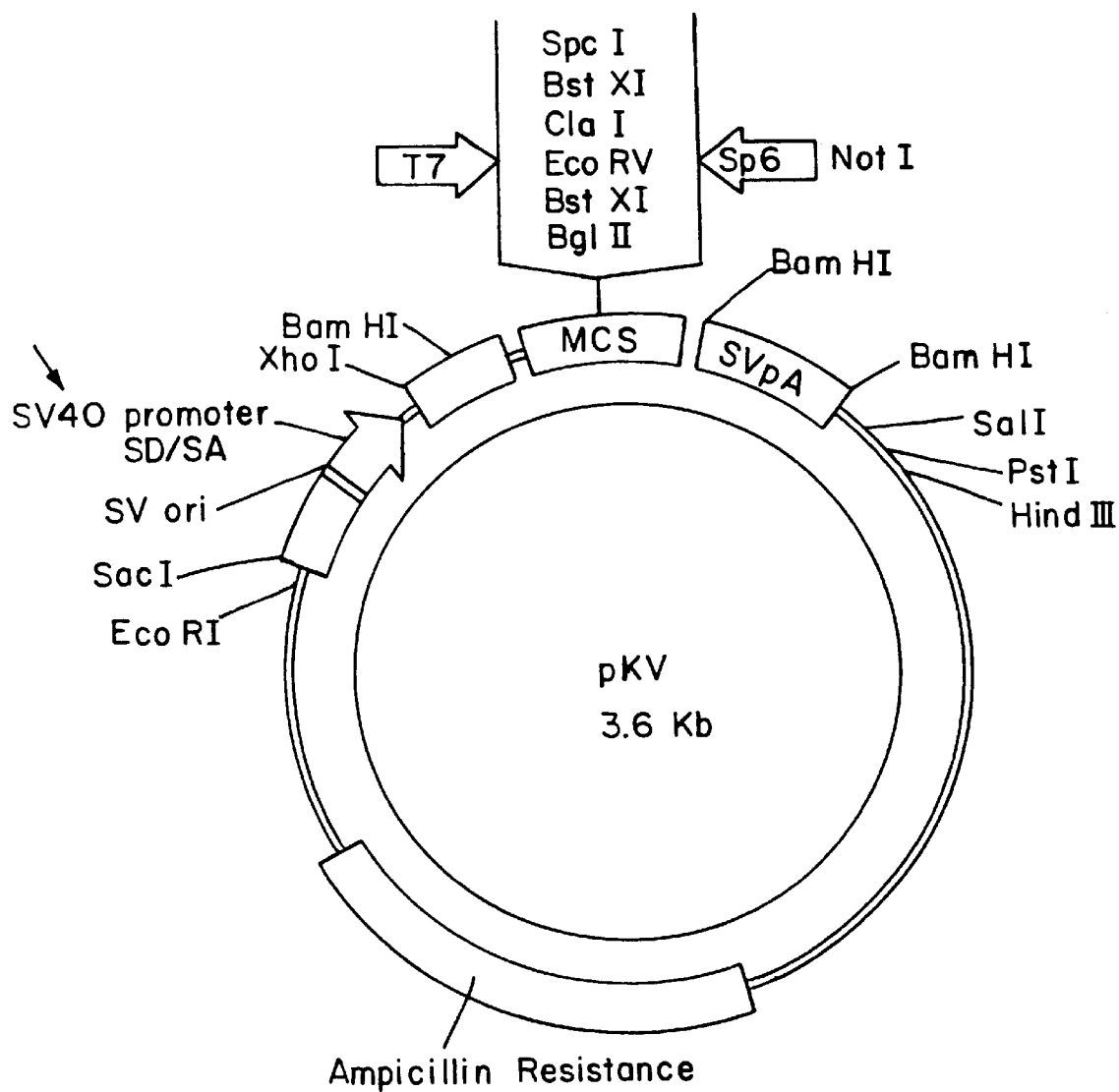

NO DNA | Wt-1 | Wt-2 | NS3 MUTANT +NS3 (1-180) | NS3 MUTANT

← FUSION PROTEIN
← NS3
← NS3(1-180)

NO DNA | Wt-1 | Wt-2 | NS3 MUTANT +NS3 | NS3 MUTANT

← FUSION PROTEIN
← IL-1B

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 9401 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: mat_peptide
        ( B ) LOCATION: 3420..5312
        ( D ) OTHER INFORMATION: /product="NS3 protease"

( i x ) FEATURE:
        ( A ) NAME/KEY: mat_peptide
        ( B ) LOCATION: 5313..5474
        ( D ) OTHER INFORMATION: /product="NS4A"

( i x ) FEATURE:
        ( A ) NAME/KEY: mat_peptide
        ( B ) LOCATION: 5475..5552
        ( D ) OTHER INFORMATION: /product="truncated NS4B"

( x i ) SEQUENCE DESCRIPTION: SEQ ID NO:1:

```
GCCAGCCCCC   TGATGGGGGC   GACACTCCAC   CATAGATCAC   TCCCCTGTGA   GGAACTACTG        60
TCTTCACGCA   GAAAGCGTCT   AGCCATGGCG   TTAGTATGAG   TGTCGTGCAG   CCTCCAGGAC       120
CCCCCCTCCC   GGGAGAGCCA   TAGTGGTCTG   CGGAACCGGT   GAGTACACCG   GAATTGCCAG       180
GACGACCGGG   TCCTTTCTTG   GATAAACCCG   CTCAATGCCT   GGAGATTTGG   GCGTGCCCCC       240
GCAAGACTGC   TAGCCGAGTA   GTGTTGGGTC   GCGAAAGGCC   TTGTGGTACT   GCCTGATAGG       300
GTGCTTGCGA   GTGCCCCGGG   AGGTCTCGTA   GACCGTGCAC   CATGAGCACG   AATCCTAAAC       360
CTCAAAGAAA   AACCAAACGT   AACACCAACC   GTCGCCCACA   GGACGTCGAG   TTCCCGGGTG       420
GCGGTCAGAT   CGTTGGTGGA   GTTTACTTGT   TGCCGCGCAG   GGGCCCTAGA   TTGGGTGTGC       480
GCGCGACGAG   GAAGACTTCC   GAGCGGTCGC   AACCTCGTGG   TAGACGTCAG   CCTATCCCCA       540
AGGCACGTCG   GCCCGAGGGC   AGGACCTGGG   CTCAGCCCGG   GTACCCTTGG   CCCCTCTATG       600
GCAATGAGGG   TTGCGGGTGG   GCGGGATGGC   TCCTGTCTCC   CCGTGGCTCT   CGGCCTAGCT       660
GGGGCCCCAC   AGACCCCCGG   CGTAGGTCGC   GCAATTTGGG   TAAGGTCATC   GATACCCTTA       720
CGTGCGGCTT   CGCCGACCTC   ATGGGGTACA   TACCGCTCGT   CGGCGCCCCT   CTTGGAGGCG       780
CTGCCAGGGC   CCTGGCGCAT   GGCGTCCGGG   TTCTGGAAGA   CGGCGTGAAC   TATGCAACAG       840
GGAACCTTCC   TGGTTGCTCT   TTCTCTATCT   TCCTTCTGGC   CCTGCTCTCT   TGCCTGACTG       900
TGCCCGCTTC   AGCCTACCAA   GTGCGCAATT   CCTCGGGGCT   TTACCATGTC   ACCAATGATT       960
```

-continued

```
GCCCTAATTC GAGTATTGTG TACGAGGCGG CCGATGCCAT CCTGCACACT CCGGGGTGTG      1020
TCCCTTGCGT TCGCGAGGGT AACGCCTCGA GGTGTTGGGT GGCGGTGACC CCCACGGTGG      1080
CCACCAGGGA CGGCAAACTC CCCACAACGC AGCTTCGACG TCATATCGAT CTGCTTGTCG      1140
GGAGCGCCAC CCTCTGCTCA GCCCTCTACG TGGGGACCT  GTGCGGGTCT GTTTTCTTG       1200
TTGGTCAACT GTTTACCTTC TCTCCCAGGC GCCACTGGAC GACGCAAAGC TGCAATTGTT      1260
CTATCTATCC CGGCCATATA ACGGGTCATC GCATGGCATG GGATATGATG ATGAACTGGT      1320
CCCCTACGGC AGCGTTGGTG GTAGCTCAGC TGCTCCGGAT CCCACAAGCC ATCATGGACA      1380
TGATCGCTGG TGCTCACTGG GGAGTCCTGG CGGGCATAGC GTATTCTCC  ATGGTGGGA       1440
ACTGGGCGAA GGTCCTGGTA GTGCTGCTGC TATTTGCCGG CGTCGACGCG GAAACCCACG      1500
TCACCGGGGG AAGTGCCGGC CACACCACGG CTGGGCTTGT TGGTCTCCTT ACACCAGGCG      1560
CCAAGCAGAA CATCCAACTG ATCAACACCA ACGGCAGTTG GCACATCAAT GCACGGCCT       1620
TGAACTGCAA CGATAGCCTT ACCACCGGCT GGTTAGCAGG GCTCTTCTAT CGCCACAAAT      1680
TCAACTCTTC AGGCTGTCCT GAGAGGTTGG CCAGCTGCCG ACGCCTTACC GATTTTGCCC      1740
AGGGCTGGGG TCCCATCAGT TATGCCAACG GAAGCGGCCT TGACGAACGC CCCTACTGTT      1800
GGCACTACCC TCCAAGACCT TGTGGCATTG TGCCCGCAAA GAGCGTGTGT GGCCCGGTAT      1860
ATTGCTTCAC TCCCAGCCCC GTGGTGGTGG GAACGACCGA CAGGTCGGGC GCGCCTACCT      1920
ACAGCTGGGG TGCAAATGAT ACGGATGTCT TCGTCCTTAA CAACACCAGG CCACCGCTGG      1980
GCAATTGGTT CGGTTGTACC TGGATGAACT CAACTGGATT CACCAAAGTG TGCGGAGCGC      2040
CCCCTTGTGT CATCGGAGGG GTGGGCAACA ACACCTTGCT CTGCCCCACT GATTGCTTCC      2100
GCAAACATCC GGAAGCCACA TACTCTCGGT GCGGCTCCGG TCCCTGGATT ACACCCAGGT      2160
GCATGGTCGA CTACCCGTAT AGGCTTTGGC ACTATCCTTG TACTATCAAT TACACCATAT      2220
TCAAAGTCAG GATGTACGTG GGAGGGGTCG AGCACAGGCT GGAAGCGGCC TGCAACTGGA      2280
CGCGGGGCGA ACGCTGTGAT CTGGAAGACA GGGACAGGTC CGAGCTCAGC CCATTGCTGC      2340
TGTCCACCAC ACAGTGGCAG GTCCTTCCGT GTTCTTTCAC GACCCTGCCA GCCTTGTCCA      2400
CCGGCCTCAT CCACCTCCAC CAGAACATTG TGGACGTGCA GTACTTGTAC GGGGTGGGGT      2460
CAAGCATCGC GTCCTGGGCC ATTAAGTGGG AGTACGTCGT TCTCCTGTTC CTTCTGCTTG      2520
CAGACGCGCG CGTCTGCTCC TGCTTGTGGA TGATGTTACT CATATCCCAA GCGGAGGCGG      2580
CTTTGGAGAA CCTCGTAATA CTCAATGCAG CATCCCTGGC CGGGACGCAC GGTCTTGTGT      2640
CCTTCCTCGT GTTCTTCTGC TTTGCGTGGT ATCTGAAGGG TAGGTGGGTG CCCGGAGCGG      2700
TCTACGCCTT CTACGGGATG TGGCCTCTCC TCCTGCTCCT GCTGGCGTTG CCTCAGCGGG      2760
CATACGCACT GGACACGGAG GTGGCCGCGT CGTGTGGCGG CGTTGTTCTT GTCGGGTTAA      2820
TGGCGCTGAC TCTGTCACCA TATTACAAGC GCTATATCAG CTGGTGCATG TGGTGGCTTC      2880
AGTATTTTCT GACCAGAGTA GAAGCGCAAC TGCACGTGTG GGTTCCCCCC CTCAACGTCC      2940
GGGGGGGGCG CGATGCCGTC ATCTTACTCA TGTGTGTTGT ACACCCGACT CTGGTATTTG      3000
ACATCACCAA ACTACTCCTG GCCATCTTCG GACCCCTTTG GATTCTTCAA GCCAGTTTGC      3060
TTAAAGTCCC CTACTTCGTG CGCGTTCAAG GCCTTCTCCG GATCTGCGCG CTAGCGCGGA      3120
AGATAGCCGG AGGTCATTAC GTGCAAATGG CCATCATCAA GTTGGGGGCG CTTACTGGCA      3180
CCTATGTGTA TAACCATCTC ACCCCTCTTC GAGACTGGGC GCACAACGGC CTGCGAGATC      3240
TGGCCGTGGC TGTGGAACCA GTCGTCTTCT CCCGAATGGA GACCAAGCTC ATCACGTGGG      3300
GGGCAGATAC CGCCGCGTGC GGTGACATCA TCAACGGCTT GCCCGTCTCT GCCCGTAGGG      3360
```

| | | | | | | |
|---|---|---|---|---|---|---|
| GCCAGGAGAT | ACTGCTTGGA | CCAGCCGACG | GAATGGTCTC | CAAGGGGTGG | AGGTTGCTGG | 3420 |
| CGCCCATCAC | GGCGTACGCC | CAGCAGACGA | GAGGCCTCCT | AGGGTGTATA | ATCACCAGCC | 3480 |
| TGACTGGCCG | GGACAAAAAC | CAAGTGGAGG | GTGAGGTCCA | GATCGTGTCA | ACTGCTACCC | 3540 |
| AAACCTTCCT | GGCAACGTGC | ATCAATGGGG | TATGCTGGAC | TGTCTACCAC | GGGGCCGGAA | 3600 |
| CGAGGACCAT | CGCATCACCC | AAGGGTCCTG | TCATCCAGAT | GTATACCAAT | GTGGACCAAG | 3660 |
| ACCTTGTGGG | CTGGCCCGCT | CCTCAAGGTT | CCCGCTCATT | GACACCCTGC | ACCTGCGGCT | 3720 |
| CCTCGGACCT | TTACCTGGTT | ACGAGGCACG | CCGACGTCAT | TCCCGTGCGC | CGGCGAGGTG | 3780 |
| ATAGCAGGGG | TAGCCTGCTT | TCGCCCCGGC | CCATTTCCTA | CCTAAAAGGC | TCCTCGGGGG | 3840 |
| GTCCGCTGTT | GTGCCCCGCG | GGACACGCCG | TGGGCCTATT | CAGGGCCGCG | TGTGCACCC | 3900 |
| GTGGAGTGAC | CAAGGCGGTG | GACTTTATCC | CTGTGGAGAA | CCTAGAGACA | ACCATGAGAT | 3960 |
| CCCCGGTGTT | CACGGACAAC | TCCTCTCCAC | CAGCAGTGCC | CCAGAGCTTC | CAGGTGGCCC | 4020 |
| ACCTGCATGC | TCCCACCGGC | AGTGGTAAGA | GCACCAAGGT | CCCGGCTGCG | TACGCAGCCC | 4080 |
| AGGGCTACAA | GGTGTTGGTG | CTCAACCCCT | CTGTTGCTGC | AACGCTGGGC | TTTGGTGCTT | 4140 |
| ACATGTCCAA | GGCCCATGGG | GTCGATCCTA | ATATCAGGAC | CGGGGTGAGA | ACAATTACCA | 4200 |
| CTGGCAGCCC | CATCACGTAC | TCCACCTACG | GCAAGTTCCT | TGCCGACGGC | GGGTGCTCAG | 4260 |
| GAGGCGCTTA | TGACATAATA | ATTTGTGACG | AGTGCCACTC | CACGGATGCC | ACATCCATCT | 4320 |
| TGGGCATCGG | CACTGTCCTT | GACCAAGCAG | AGACTGCGGG | GGCGAGATTG | GTTGTGCTCG | 4380 |
| CCACTGCTAC | CCCTCCGGGC | TCCGTCACTG | TGTCCCATCC | TAACATCGAG | GAGGTTGCTC | 4440 |
| TGTCCACCAC | CGGAGAGATC | CCTTTCTACG | GCAAGGCTAT | CCCCCTCGAG | GTGATCAAGG | 4500 |
| GGGAAGACA | TCTCATCTTC | TGTCACTCAA | AGAAGAAGTG | CGACGAGCTC | GCCGCGAAGC | 4560 |
| TGGTCGCATT | GGGCATCAAT | GCCGTGGCCT | ACTACCGCGG | ACTTGACGTG | TCTGTCATCC | 4620 |
| CGACCAACGG | CGATGTTGTC | GTCGTGTCGA | CCGATGCTCT | CATGACTGGC | TTTACCGGCG | 4680 |
| ACTTCGACTC | TGTGATAGAC | TGCAACACGT | GTGTCACTCA | GACAGTCGAT | TTCAGCCTTG | 4740 |
| ACCCTACCTT | TACCATTGAG | ACAACCACGC | TCCCCAGGA | TGCTGTCTCC | AGGACTCAGC | 4800 |
| GCCGGGGCAG | GACTGGCAGG | GGGAAGCCAG | GCATCTACAG | ATTTGTGGCA | CCGGGGGAGC | 4860 |
| GCCCCTCCGG | CATGTTCGAC | TCGTCCGTCC | TCTGTGAGTG | CTATGACGCG | GGCTGTGCTT | 4920 |
| GGTATGAGCT | CATGCCCGCC | GAGACTACAG | TTAGGCTACG | AGCGTACATG | AACACCCCGG | 4980 |
| GCTTCCCGT | GTGCCAGGAC | CATCTTGAAT | TTTGGGAGGG | CGTCTTTACG | GGCCTCACCC | 5040 |
| ATATAGATGC | CCACTTTCTA | TCCCAGACAA | AGCAGAGTGG | GGAGAACTTT | CCTTACCTGG | 5100 |
| TAGCGTACCA | AGCCACCGTG | TGCGCTAGGG | CTCAAGCCCC | TCCCCCATCG | TGGGACCAGA | 5160 |
| TGTGGAAGTG | TTTGATCCGC | CTTAAACCCA | CCCTCCATGG | GCCAACACCC | CTGCTATACA | 5220 |
| GACTGGGCGC | TGTTCAGAAT | GAAGTCACCC | TGACGCACCC | AATCACCAAA | TACATCATGA | 5280 |
| CATGCATGTC | GGCCGACCTG | GAGGTCGTCA | CGAGCACCTG | GGTGCTCGTT | GGCGGCGTCC | 5340 |
| TGGCTGCTCT | GGCCGCGTAT | TGCCTGTCAA | CAGGCTGCGT | GGTCATAGTG | GCAGGATTG | 5400 |
| TCTTGTCCGG | GAAGCCGGCA | ATTATACCTG | ACAGGAGGT | TCTCTACCAG | GAGTTCGATG | 5460 |
| AGATGGAAGA | GTGCTCTCAG | CACTTACCGT | ACATCGAGCA | AGGGATGATG | CTCGCTGAGC | 5520 |
| AGTTCAAGCA | GAAGGCCCTC | GGCCTCCTGC | AGACCGCGTC | CCGCCATGCA | GAGGTTATCA | 5580 |
| CCCCTGCTGT | CCAGACCAAC | TGGCAGAAAC | TCGAGGTCTT | CTGGGCGAAG | CACATGTGGA | 5640 |
| ATTTCATCAG | TGGGATACAA | TATTTGGCGG | GCCTGTCAAC | GCTGCCTGGT | AACCCCGCCA | 5700 |
| TTGCTTCATT | GATGGCTTTT | ACAGCTGCCG | TCACCAGCCC | ACTAACCACT | GGCCAAACCC | 5760 |

-continued

| | | | | | |
|---|---|---|---|---|---|
| TCCTCTTCAA | CATATTGGGG | GGGTGGGTGG | CTGCCCAGCT | CGCCGCCCCC | GGTGCCGCTA | 5820 |
| CCGCCTTTGT | GGGCGCTGGC | TTAGCTGGCG | CCGCCATCGG | CAGCGTTGGA | CTGGGGAAGG | 5880 |
| TCCTCGTGGA | CATTCTTGCA | GGGTATGGCG | CGGGCGTGGC | GGGAGCTCTT | GTAGCATTCA | 5940 |
| AGATCATGAG | CGGTGAGGTC | CCCTCCACGG | AGGACCTGGT | CAATCTGCTG | CCCGCCATCC | 6000 |
| TCTCGCCTGG | AGCCCTTGTA | GTCGGTGTGG | TCTGCGCAGC | AATACTGCGC | CGGCACGTTG | 6060 |
| GCCCGGGCGA | GGGGGCAGTG | CAATGGATGA | ACCGGCTAAT | AGCCTTCGCC | TCCCGGGGGA | 6120 |
| ACCATGTTTC | CCCCACGCAC | TACGTGCCGG | AGAGCGATGC | AGCCGCCCGC | GTCACTGCCA | 6180 |
| TACTCAGCAG | CCTCACTGTA | ACCCAGCTCC | TGAGGCGACT | ACATCAGTGG | ATAAGCTCGG | 6240 |
| AGTGTACCAC | TCCATGCTCC | GGCTCCTGGC | TAAGGGACAT | CTGGGACTGG | ATATGCGAGG | 6300 |
| TGCTGAGCGA | CTTTAAGACC | TGGCTGAAAG | CCAAGCTCAT | GCCACAACTG | CCTGGGATTC | 6360 |
| CCTTTGTGTC | CTGCCAGCGC | GGGTATAGGG | GGGTCTGGCG | AGGAGACGGC | ATTATGCACA | 6420 |
| CTCGCTGCCA | CTGTGGAGCT | GAGATCACTG | GACATGTCAA | AAACGGGACG | ATGAGGATCG | 6480 |
| TCGGTCCTAG | GACCTGCAGG | AACATGTGGA | GTGGGACGTT | CCCCATTAAC | GCCTACACCA | 6540 |
| CGGGCCCCTG | TACTCCCCTT | CCTGCGCCGA | ACTATAAGTT | CGCGCTGTGG | AGGGTGTCTG | 6600 |
| CAGAGGAATA | CGTGGAGATA | AGGCGGGTGG | GGGACTTCCA | CTACGTATCG | GGTATGACTA | 6660 |
| CTGACAATCT | TAAATGCCCG | TGCCAGATCC | CATCGCCCGA | ATTTTTCACA | GAATTGGACG | 6720 |
| GGGTGCGCCT | ACATAGGTTT | GCGCCCCCTT | GCAAGCCCTT | GCTGCGGGAG | GAGGTATCAT | 6780 |
| TCAGAGTAGG | ACTCCACGAG | TACCCGGTGG | GGTCGCAATT | ACCTTGCGAG | CCCGAACCGG | 6840 |
| ACGTAGCCGT | GTTGACGTCC | ATGCTCACTG | ATCCCTCCCA | TATAACAGCA | GAGGCGGCCG | 6900 |
| GGAGAAGGTT | GGCGAGAGGG | TCACCCCCTT | CTATGGCCAG | CTCCTCGGCC | AGCCAGCTGT | 6960 |
| CCGCTCCATC | TCTCAAGGCA | ACTTGCACCG | CCAACCATGA | CTCCCCTGAC | GCCGAGCTCA | 7020 |
| TAGAGGCTAA | CCTCCTGTGG | AGGCAGGAGA | TGGGCGGCAA | CATCACCAGG | GTTGAGTCAG | 7080 |
| AGAACAAAGT | GGTGATTCTG | GACTCCTTCG | ATCCGCTTGT | GGCAGAGGAG | GATGAGCGGG | 7140 |
| AGGTCTCCGT | ACCCGCAGAA | ATTCTGCGGA | AGTCTCGGAG | ATTCGCCCGG | GCCCTGCCCG | 7200 |
| TTTGGGCGCG | GCCGGACTAC | AACCCCCGC | TAGTAGAGAC | GTGGAAAAAG | CCTGACTACG | 7260 |
| AACCACCTGT | GGTCCATGGC | TGCCCGCTAC | CACCTCCACG | GTCCCTCCT | GTGCCTCCGC | 7320 |
| CTCGGAAAAA | GCGTACGGTG | GTCCTCACCG | AATCAACCCT | ACCTACTGCC | TTGGCCGAGC | 7380 |
| TTGCCACCAA | AAGTTTTGGC | AGCTCCTCAA | CTTCCGGCAT | TACGGGCGAC | AATATGACAA | 7440 |
| CATCCTCTGA | GCCCGCCCCT | TCTGGCTGCC | CCCCCGACTC | CGACGTTGAG | TCCTATTCTT | 7500 |
| CCATGCCCCC | CCTGGAGGGG | GAGCCTGGGG | ATCCGGATTT | CAGCGACGGG | TCATGGTCGA | 7560 |
| CGGTCAGTAG | TGGGGCCGAC | ACGGAAGATG | TCGTGTGCTG | CTCAATGTCT | TATACCTGGA | 7620 |
| CAGGCGCACT | CGTCACCCCG | TGCGCTGCGG | AAGAACAAAA | ACTGCCCATC | AACGCACTGA | 7680 |
| GCAACTCGTT | GCTACGCCAT | CACAATCTGG | TATATTCCAC | CACTTCACGC | AGTGCTTGCC | 7740 |
| AAAGGCAGAA | GAAAGTCACA | TTTGACAGAC | TGCAAGTTCT | GGACAGCCAT | TACCAGGACG | 7800 |
| TGCTCAAGGA | GGTCAAAGCA | GCGGCGTCAA | AAGTGAAGGC | TAACTTGCTA | TCCGTAGAGG | 7860 |
| AAGCTTGCAG | CCTGACGCCC | CCACATTCAG | CCAAATCCAA | GTTTGGCTAT | GGGGCAAAAG | 7920 |
| ACGTCCGTTG | CCATGCCAGA | AAGGCCGTAG | CCCACATCAA | CTCCGTGTGG | AAAGACCTTC | 7980 |
| TGGAAGACAG | TGTAACACCA | ATAGACACTA | TCATCATGGC | CAAGAACGAG | GTCTTCTGCG | 8040 |
| TTCAGCCTGA | GAAGGGGGGT | CGTAAGCCAG | CTCGTCTCAT | CGTGTTCCCC | GACCTGGGCG | 8100 |
| TGCGCGTGTG | CGAGAAGATG | GCCCTGTACG | ACGTGGTTAG | CAAACTCCCC | CTGGCCGTGA | 8160 |

| | | | | | | |
|---|---|---|---|---|---|---|
| TGGGAAGCTC | CTACGGATTC | CAATACTCAC | CAGGACAGCG | GGTTGAATTC | CTCGTGCAAG | 8220 |
| CGTGGAAGTC | CAAGAAGACC | CCGATGGGGT | TCCCGTATGA | TACCCGCTGT | TTTGACTCCA | 8280 |
| CAGTCACTGA | GAGCGACATC | CGTACGGAGG | AGGCAATTTA | CCAATGTTGT | GACCTGGACC | 8340 |
| CCCAAGCCCG | CGTGGCCATC | AAGTCCCTCA | CTGAGAGGCT | TTATGTTGGG | GGCCCTCTTA | 8400 |
| CCAATTCAAG | GGGGGAAAAC | TGCGGCTATC | GCAGGTGCCG | CGCGAGCGGC | GTACTGACAA | 8460 |
| CTAGCTGTGG | TAACACCCTC | ACTTGCTACA | TCAAGGCCCG | GGCAGCCCGT | CGAGCCGCAG | 8520 |
| GGCTCCAGGA | CTGCACCATG | CTCGTGTGTG | GCGACGACTT | AGTCGTTATC | TGTGAAAGTG | 8580 |
| CGGGGGTCCA | GGAGGACGCG | GCGAGCCTGA | GAGCCTTTAC | GGAGGCTATG | ACCAGGTACT | 8640 |
| CCGCCCCCCC | CGGGGACCCC | CCACAACCAG | AATACGACTT | GGAGCTTATA | ACATCATGCT | 8700 |
| CCTCCAACGT | GTCAGTCGCC | CACGACGGCG | CTGGAAAAAG | GGTCTACTAC | CTTACCCGTG | 8760 |
| ACCCTACAAC | CCCCCTCGCG | AGAGCCGCGT | GGGAGACAGC | AAGACACACT | CCAGTCAATT | 8820 |
| CCTGGCTAGG | CAACATAATC | ATGTTTGCCC | CCACACTGTG | GGCGAGGATG | ATACTGATGA | 8880 |
| CCCATTTCTT | TAGCGTCCTC | ATAGCCAGGG | ATCAGCTTGA | ACAGGCTCTT | AACTGTGAGA | 8940 |
| TCTACGCAGC | CTGCTACTCC | ATAGAACCAC | TGGATCTACC | TCCAATCATT | CAAAGACTCC | 9000 |
| ATGGCCTCAG | CGCATTTTTA | CTCCACAGTT | ACTCTCCAGG | TGAAGTCAAT | AGGGTGGCCG | 9060 |
| CATGCCTCAG | AAAACTTGGG | GTCCCGCCCT | TGCGAGCTTG | GAGACACCGG | GCCCGGAGCG | 9120 |
| TCCGCGCTAG | GCTTCTGTCC | AGGGGAGGCA | GGGCTGCCAT | ATGTGGCAAG | TACCTCTTCA | 9180 |
| ACTGGGCAGT | AAGAACAAAG | CTCAAACTCA | CTCCAATAGC | GGCCGCTGGC | CGGCTGGACT | 9240 |
| TGTCCGGTTG | GTTCACGGCT | GGCTACAGCG | GGGGAGACAT | TTATCACAGC | GTGTCTCATG | 9300 |
| CCCGGCCCCG | CTGGTTCTGG | TTTTGCCTAC | TCCTGCTCGC | TGCAGGGGTA | GGCATCTACC | 9360 |
| TCCTCCCCAA | CCGGTGAACG | GGGAGCTAGA | CACTCCGGCC | T | | 9401 |

( 2 ) INFORMATION FOR SEQ ID NO:2:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer"

( i i i ) HYPOTHETICAL: NO ( i v ) ANTI-SENSE: NO ( x i ) SEQUENCE DESCRIPTION: SEQ ID NO:2:

| | | | | |
|---|---|---|---|---|
| GGACTAGTCT | GCAGTCTAGA | GCTCCATGGC | GCCCATCACG | GCGTACG | 47 |

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer"

( i i i ) HYPOTHETICAL: NO ( i v ) ANTI-SENSE: NO ( x i ) SEQUENCE DESCRIPTION: SEQ ID NO:3:

```
CGGCTGCACC  TCCAGCAGTG  CATTTAGAT  CTTAAGTCTA  GAAG                    44
```

(2) INFORMATION FOR SEQ ID NO:4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(iii) HYPOTHETICAL: NO (iv) ANTI-SENSE: NO (xi) SEQUENCE DESCRIPTION: SEQ ID NO:4:

```
AAGCTACTCT  ACCTTCTCAC  GATTTAGAT  CTTAAGTCTA  GAAG                    44
```

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(iii) HYPOTHETICAL: NO (iv) ANTI-SENSE: NO (xi) SEQUENCE DESCRIPTION: SEQ ID NO:5:

```
GGATCTCTGT  TGGTACTCTA  GGATTTTAGA  TCTTAAGTCT  AGAAG                  45
```

(2) INFORMATION FOR SEQ ID NO:6:

(i) SEQUENCE CHARACTERISTICS:
        (A) LENGTH: 64 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "OLIGONUCLEOTIDE DUPLEX"

(iii) HYPOTHETICAL: NO (iv) ANTI-SENSE: NO (v) FRAGMENT TYPE: internal (ix) FEATURE:
        (A) NAME/KEY: misc_feature
        (B) LOCATION: 1..4
        (D) OTHER INFORMATION: /product="SINGLE STRANDED REGION
            ON CODING STRAND"

(ix) FEATURE:
        (A) NAME/KEY: misc_feature
        (B) LOCATION: 61..64
        (D) OTHER INFORMATION: /product="SINGLE STRANDED REGION
            ON COMPLEMENTARY STRAND"

(xi) SEQUENCE DESCRIPTION: SEQ ID NO:6:

```
TGCACGGCGC  CGACACGGAA  GATGTCGTGT  GCTGCTCAAT  GTCTTATACC  TGGACAGGCG    60

TGCA                                                                      64
```

(2) INFORMATION FOR SEQ ID NO:7:

(  i  ) SEQUENCE CHARACTERISTICS:
(  A  ) LENGTH: 20 amino acids
(  B  ) TYPE: amino acid
(  C  ) STRANDEDNESS: single
(  D  ) TOPOLOGY: linear (  i i  ) MOLECULE TYPE: peptide (  i i i  ) HYPOTHETICAL: NO (  v  ) FRAGMENT TYPE: internal (  x i  ) SEQUENCE DESCRIPTION: SEQ ID NO:7:

```
Gly  Ala  Asp  Thr  Glu  Asp  Val  Val  Cys  Cys  Ser  Met  Ser  Tyr  Thr  Trp
 1                    5                        10                       15
Thr  Gly  Val  His
              20
```

( 2 ) INFORMATION FOR SEQ ID NO:8:

(  i  ) SEQUENCE CHARACTERISTICS:
(  A  ) LENGTH: 47 base pairs
(  B  ) TYPE: nucleic acid
(  C  ) STRANDEDNESS: single
(  D  ) TOPOLOGY: linear (  i i  ) MOLECULE TYPE: other nucleic acid
(  A  ) DESCRIPTION: /desc = "oligonucleotide primer"

(  i i i  ) HYPOTHETICAL: NO (  i v  ) ANTI-SENSE: NO (  x i  ) SEQUENCE DESCRIPTION: SEQ ID NO:8:

```
GGACTAGTCT  GCAGTCTAGA  GCTCCATGGC  GCCCATCACG  GCGTACG                                    47
```

( 2 ) INFORMATION FOR SEQ ID NO:9:

(  i  ) SEQUENCE CHARACTERISTICS:
(  A  ) LENGTH: 27 base pairs
(  B  ) TYPE: nucleic acid
(  C  ) STRANDEDNESS: single
(  D  ) TOPOLOGY: linear (  i i  ) MOLECULE TYPE: other nucleic acid
(  A  ) DESCRIPTION: /desc = "oligonucleotide primer"

(  i i i  ) HYPOTHETICAL: NO (  i v  ) ANTI-SENSE: NO (  x i  ) SEQUENCE DESCRIPTION: SEQ ID NO:9:

```
CGGGAGCCGG  AGGACGTCTG  GCGCAGG                                                            27
```

( 2 ) INFORMATION FOR SEQ ID NO:10:

(  i  ) SEQUENCE CHARACTERISTICS:
(  A  ) LENGTH: 1497 base pairs
(  B  ) TYPE: nucleic acid
(  C  ) STRANDEDNESS: double
(  D  ) TOPOLOGY: linear (  i i  ) MOLECULE TYPE: cDNA (  i i i  ) HYPOTHETICAL: NO (  i v  ) ANTI-SENSE: NO (  i x  ) FEATURE:
(  A  ) NAME/KEY: CDS
(  B  ) LOCATION: 87..893

( i x ) FEATURE:
   ( A ) NAME/KEY: misc_feature
   ( B ) LOCATION: 426..427
   ( D ) OTHER INFORMATION: /label=ApaLIsite ( x i ) SEQUENCE DESCRIPTION: SEQ ID NO:10:

```
ACCAACCTCT TCGAGGCACA AGGCACAACA GGCTGCTCTG GGATTCTCTT CAGCCAATCT           60

TCATTGCTCA AGTGTCTGAA GCAGCC ATG GCA GAA GTA CCT GAG CTC GCC AGT          113
                            Met Ala Glu Val Pro Glu Leu Ala Ser
                              1               5

GAA ATG ATG GCT TAT TAC AGT GGC AAT GAG GAT GAC TTG TTC TTT GAA           161
Glu Met Met Ala Tyr Tyr Ser Gly Asn Glu Asp Asp Leu Phe Phe Glu
 10              15              20              25

GCT GAT GGC CCT AAA CAG ATG AAG TGC TCC TTC CAG GAC CTG GAC CTC           209
Ala Asp Gly Pro Lys Gln Met Lys Cys Ser Phe Gln Asp Leu Asp Leu
             30              35              40

TGC CCT CTG GAT GGC GGC ATC CAG CTA CGA ATC TCC GAC CAC CAC TAC           257
Cys Pro Leu Asp Gly Gly Ile Gln Leu Arg Ile Ser Asp His His Tyr
             45              50              55

AGC AAG GGC TTC AGG CAG GCC GCG TCA GTT GTT GTG GCC ATG GAC AAG           305
Ser Lys Gly Phe Arg Gln Ala Ala Ser Val Val Val Ala Met Asp Lys
         60              65              70

CTG AGG AAG ATG CTG GTT CCC TGC CCA CAG ACC TTC CAG GAG AAT GAC           353
Leu Arg Lys Met Leu Val Pro Cys Pro Gln Thr Phe Gln Glu Asn Asp
     75              80              85

CTG AGC ACC TTC TTT CCC TTC ATC TTT GAA GAA GAA CCT ATC TTC TTC           401
Leu Ser Thr Phe Phe Pro Phe Ile Phe Glu Glu Glu Pro Ile Phe Phe
 90              95             100             105

GAC ACA TGG GAT AAC GAG GCT TAT GTG CAC GAT GCA CCT GTA CGA TCA           449
Asp Thr Trp Asp Asn Glu Ala Tyr Val His Asp Ala Pro Val Arg Ser
             110             115             120

CTG AAC TGC ACG CTC CGG GAC TCA CAG CAA AAA AGC TTG GTG ATG TCT           497
Leu Asn Cys Thr Leu Arg Asp Ser Gln Gln Lys Ser Leu Val Met Ser
             125             130             135

GGT CCA TAT GAA CTG AAA GCT CTC CAC CTC CAG GGA CAG GAT ATG GAG           545
Gly Pro Tyr Glu Leu Lys Ala Leu His Leu Gln Gly Gln Asp Met Glu
         140             145             150

CAA CAA GTG GTG TTC TCC ATG TCC TTT GTA CAA GGA GAA GAA AGT AAT           593
Gln Gln Val Val Phe Ser Met Ser Phe Val Gln Gly Glu Glu Ser Asn
     155             160             165

GAC AAA ATA CCT GTG GCC TTG GGC CTC AAG GAA AAG AAT CTG TAC CTG           641
Asp Lys Ile Pro Val Ala Leu Gly Leu Lys Glu Lys Asn Leu Tyr Leu
170             175             180             185

TCC TGC GTG TTG AAA GAT GAT AAG CCC ACT CTA CAG CTG GAG AGT GTA           689
Ser Cys Val Leu Lys Asp Asp Lys Pro Thr Leu Gln Leu Glu Ser Val
             190             195             200

GAT CCC AAA AAT TAC CCA AAG AAG AAG ATG GAA AAG CGA TTT GTC TTC           737
Asp Pro Lys Asn Tyr Pro Lys Lys Lys Met Glu Lys Arg Phe Val Phe
             205             210             215

AAC AAG ATA GAA ATC AAT AAC AAG CTG GAA TTT GAG TCT GCC CAG TTC           785
Asn Lys Ile Glu Ile Asn Asn Lys Leu Glu Phe Glu Ser Ala Gln Phe
             220             225             230

CCC AAC TGG TAC ATC AGC ACC TCT CAA GCA GAA AAC ATG CCC GTC TTC           833
Pro Asn Trp Tyr Ile Ser Thr Ser Gln Ala Glu Asn Met Pro Val Phe
         235             240             245

CTG GGA GGG ACC AAA GGC GGC CAG GAT ATA ACT GAC TTC ACC ATG CAA           881
Leu Gly Gly Thr Lys Gly Gly Gln Asp Ile Thr Asp Phe Thr Met Gln
250             255             260             265

TTT GTG TCT TCC TAAAGAGAGC TGTACCCAGA GAGTCCTGTG CTGAATGTGG               933
Phe Val Ser Ser
```

-continued

```
ACTCAATCCC TAGGGCTGGC AGAAAGGGAA CAGAAAGGTT TTTGAGTACG GCTATAGCCT      993
GGACTTTCCT GTTGTCTACA CCAATGCCCA ACTGCCTGCC TTAGGGTAGT GCTAAGAGGA     1053
TCTCCTGTCC ATCAGCCAGG ACAGTCAGCT CTCTCCTTTC AGGGCCAATC CCCAGCCCTT     1113
TTGTTGAGCC AGGCCTCTCT CACCTCTCCT ACTCACTTAA AGCCCGCCTG ACAGAAACCA     1173
CGGCCACATT TGGTTCTAAG AAACCCTCTG TCATTCGCTC CCACATTCTG ATGAGCAACC     1233
GCTTCCCTAT TTATTTATTT ATTTGTTTGT TTGTTTTATT CATTGGTCTA ATTTATTCAA     1293
AGGGGGCAAG AAGTAGCAGT GTCTGTAAAA GAGCCTAGTT TTTAATAGCT ATGGAATCAA     1353
TTCAATTTGG ACTGGTGTGC TCTCTTTAAA TCAAGTCCTT TAATTAAGAC TGAAAATATA     1413
TAAGCTCAGA TTATTTAAAT GGGAATATTT ATAAATGAGC AAATATCATA CTGTTCAATG     1473
GTTCTGAAAT AAACTTCTCT GAAG                                            1497
```

(2) INFORMATION FOR SEQ ID NO:11:

(i) SEQUENCE CHARACTERISTICS:
    (A) LENGTH: 269 amino acids
    (B) TYPE: amino acid
    (D) TOPOLOGY: linear (ii) MOLECULE TYPE: protein (xi) SEQUENCE DESCRIPTION: SEQ ID NO:11:

```
Met Ala Glu Val Pro Glu Leu Ala Ser Glu Met Met Ala Tyr Tyr Ser
 1               5                  10                  15
Gly Asn Glu Asp Asp Leu Phe Phe Glu Ala Asp Gly Pro Lys Gln Met
                20                  25                  30
Lys Cys Ser Phe Gln Asp Leu Asp Leu Cys Pro Leu Asp Gly Gly Ile
                35                  40                  45
Gln Leu Arg Ile Ser Asp His His Tyr Ser Lys Gly Phe Arg Gln Ala
        50                  55                  60
Ala Ser Val Val Val Ala Met Asp Lys Leu Arg Lys Met Leu Val Pro
65                  70                  75                  80
Cys Pro Gln Thr Phe Gln Glu Asn Asp Leu Ser Thr Phe Phe Pro Phe
                85                  90                  95
Ile Phe Glu Glu Glu Pro Ile Phe Phe Asp Thr Trp Asp Asn Glu Ala
                100                 105                 110
Tyr Val His Asp Ala Pro Val Arg Ser Leu Asn Cys Thr Leu Arg Asp
                115                 120                 125
Ser Gln Gln Lys Ser Leu Val Met Ser Gly Pro Tyr Glu Leu Lys Ala
        130                 135                 140
Leu His Leu Gln Gly Gln Asp Met Glu Gln Gln Val Val Phe Ser Met
145                 150                 155                 160
Ser Phe Val Gln Gly Glu Glu Ser Asn Asp Lys Ile Pro Val Ala Leu
                165                 170                 175
Gly Leu Lys Glu Lys Asn Leu Tyr Leu Ser Cys Val Leu Lys Asp Asp
                180                 185                 190
Lys Pro Thr Leu Gln Leu Glu Ser Val Asp Pro Lys Asn Tyr Pro Lys
                195                 200                 205
Lys Lys Met Glu Lys Arg Phe Val Phe Asn Lys Ile Glu Ile Asn Asn
        210                 215                 220
Lys Leu Glu Phe Glu Ser Ala Gln Phe Pro Asn Trp Tyr Ile Ser Thr
225                 230                 235                 240
Ser Gln Ala Glu Asn Met Pro Val Phe Leu Gly Gly Thr Lys Gly Gly
                245                 250                 255
```

```
Gln Asp Ile Thr Asp Phe Thr Met Gln Phe Val Ser Ser
            260                 265
```

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(iii) HYPOTHETICAL: NO (iv) ANTI-SENSE: NO (xi) SEQUENCE DESCRIPTION: SEQ ID NO:12:

```
CTCGGCCTCC  TGCAGGCACC  TGTACGATCA  CTGAAC                          36
```

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(iii) HYPOTHETICAL: NO (iv) ANTI-SENSE: NO (xi) SEQUENCE DESCRIPTION: SEQ ID NO:13:

```
GTTAAACACA  GAAGGATTTT  AGATCTTAAG  GG                              32
```

METHODS, NUCLEOTIDE SEQUENCES AND HOST CELLS FOR ASSAYING EXOGENOUS AND ENDOGENOUS PROTEASE ACTIVITY

TECHNICAL FIELD OF INVENTION

The invention relates to methods for assaying exogenous protease activity in a host cell transformed with nucleotide sequences encoding that protease and a specialized substrate. It also relates to methods for assaying endogenous protease activity in a host cell transformed with nucleotide sequences encoding a specialized substrate. When these nucleotide sequences are expressed, the exogenous or endogenous protease cleaves the substrate and releases a polypeptide that is secreted out of the cell, where it can be easily quantitated using standard assays. The methods and transformed host cells of this invention are particularly useful for identifying inhibitors of the exogenous and endogenous proteases. If the protease is a protease from an infectious agent or is characteristic of a diseased state, inhibitors identified by these methods are potential pharmaceutical agents for treatment or prevention of the disease.

BACKGROUND ART

Proteases play an important role in the regulation of many biological processes. They also play a major role in disease. In particular, proteolysis of primary polypeptide precursors is essential to the replication of several infectious viruses, including HIV and HCV. These viruses encode proteins that are initially synthesized as large polyprotein precursors Those precursors are ultimately processed by the viral protease to mature viral proteins. In light of this, researchers have begun to concentrate on inhibition of viral proteases as a potential treatment for certain viral diseases.

Proteases also play a role in non-infectious diseases. For example, changes in normal cellular function may cause an undesirable increase or decrease in proteolytic activity. This often leads to a disease state.

The ability to detect viral or mutant protease activity in a quick and simple assay is important in the biochemical characterization of these proteases and in the screening and identification of potential inhibitors. Several of these assays have been described in the art.

T. M. Block et al., *Antimicrob. Agents Chemother.*, 34, pp. 2337–41 (1990) described a prototype assay for screening potential HIV protease inhibitors. This assay involved cloning the HIV protease recognition sequence into the tetracycline resistance gene ($Tet^R$) of pBR322 and cotransfroming *E. coli* with the modified $Tet^R$ gene and the gene encoding the HIV protease. Coexpression of these two genes caused tetracycline sensitivity. Potential inhibitors were identified by the ability to restore tetracycline resistance to the transformed bacteria.

E. Sarubbi et al., *FEBS Lett.*, 279, pp. 265–69 (1991) described another assay for detecting HIV protease inhibitors that utilized a HIV-1 Gag-β-galactosidase fusion protein and a monoclonal antibody that bound to the fusion protein in the gag region. Coexpression of the HIV protease and the fusion protein lead to cleavage of the latter and abolished monoclonal antibody binding. Potential inhibitors were identified by increased binding of the monoclonal antibody to the fusion protein.

T. A. Smith et al., *Proc. Natl. Acad. Sci. USA*, 88, pp. 5159–62 (1991), B. Dasmahapatra et al., *Proc. Natl. Acad. Sci. USA*, 89, pp. 4159–62 (1992) and M. G. Murray et al., *Gene*, 134, pp. 123–28 (1993) each described protease assay systems utilizing the yeast GAL4 protein. Each of these authors described inserting a protease cleavage site in between the DNA binding domain and the transcriptional activating domain of GAL4. Cleavage of that site by a coexpressed protease renders GAL4 transcriptionally inactive leading to the inability of the transformed yeast to metabolize galactose.

H.-D. Liebig et al., *Proc. Natl. Acad. Sci. USA*, 88, pp. 5979–83 (1991) disclosed the use of a fusion protein consisting of a self-cleaving protease fused to the a fragment of β-galactosidase to assay protease activity. Active forms of the protease cleaved themselves off of the fusion protein and the resulting protein was able to carry out α-complementation. Fusions containing inactive protease were unable to perform α-complementation.

Y. Komoda et al., *J. Virol.*, 68, pp. 7351–57 (1994) described an assay to identify HCV protease cleavage sites within the HCV precursor polyprotein. These authors created chimeric proteins comprising various portions of the HCV precursor polyprotein inserted in between the *E. coli* maltose binding protein and dihydrofolate reductase. If the HCV portion of these chimeras contained a cleavage site, the chimera would be cleaved when it was coexpressed with HCV protease in *E. coli*. Cleavage of the chimera was determined by SDS-polyacrylamide gel electrophoresis of *E. coli* lysates.

Y. Hirowatari et al., *Anal. Biochem.*, 225, pp. 113–120 (1995) described another assay to detect HCV protease activity. In this assay, the substrate, HCV protease and a reporter gene are cotransfected into COS cells. The substrate is a fusion protein consisting of (HCV NS2)-(DHFR)-(HCV NS3 cleavage site)-Tax1. The reporter gene is chloramphenicol transferase (CAT) under control of the HTLV-1 long terminal repeat (LTR) and resides in the cell nucleus following expression. The uncleaved substrate is expressed as a membrane-bound protein on the surface of the endoplasmic reticulum due to the HCV NS2 portion. Upon cleavage, the released Tax1 protein translocates to the nucleus and activates CAT expression by binding to the HTLV-1 LTR. Protease activity is determined by measuring CAT activity in a cell lysate.

Despite these developments, no one has yet developed a protease assay system that can be carried out with higher eukaryotic cells and is both quantitative and does not require cell lysis prior to quantitation. Avoiding cell lysis prior to quantitation is desirable in that the assay may be performed more rapidly and with less manipulation. Also, lysis can often lead to aberrant results. Thus, there is a need for an accurate and quantitative cellular-based protease assay that can be carried out in a higher eukaryotic cell without cell lysis.

SUMMARY OF THE INVENTION

The present invention fulfills this need by providing methods for assaying exogenous protease activity in a host cell expressing that protease. The methods involve utilizing a host cell expressing a first nucleotide sequence encoding an exogenous protease and a second nucleotide sequence encoding an artificial substrate for that protease. The artificial substrate comprises a cleavage site for the protease situated at or near the natural maturation site of a prepolypeptide, part of which is secreted following proteolytic processing. When the host is grown under conditions that cause expression of the first and second nucleotide sequences, the exogenous protease cuts the artificial substrate at the cleavage site, releasing the mature polypeptide which is secreted into the growth media. The growth media is then isolated and assayed for the mature polypeptide.

Alternatively, the invention may be utilized to assay endogenous proteases, especially when quantitation of those proteases is difficult due to the inability to detect or distinguish between the cleaved and uncleaved native substrate.

According to one aspect of the invention, the assay is used to quantitate an exogenous viral protease. Such assays are particularly useful as replacements for current viral protease assays that require the use of intact, infectious virus or where no simple viral model is available to detect viral protease activity. These assays may be used to identify and assay potential inhibitors of viral proteases which, in turn, may be used as pharmaceutical agents for the treatment or prevention of viral disease.

This invention also provides host cells transformed with nucleotide sequences encoding an endogenous protease and a corresponding substrate, as well as those transformed with a specialized substrate for an endogenous protease. These hosts may be used in the methods of this invention.

BRIEF DESCRIPTION OF THE DRAWINGS

FIG. 2 depicts the structure of a derivative of pKV containing the pre-IL-1β coding sequence.

FIG. 3, panel B, is an immunoblot of the same cell lysates probed with an anti-IL-1β antibody.

DETAILED DESCRIPTION OF THE INVENTION

Figure 1:
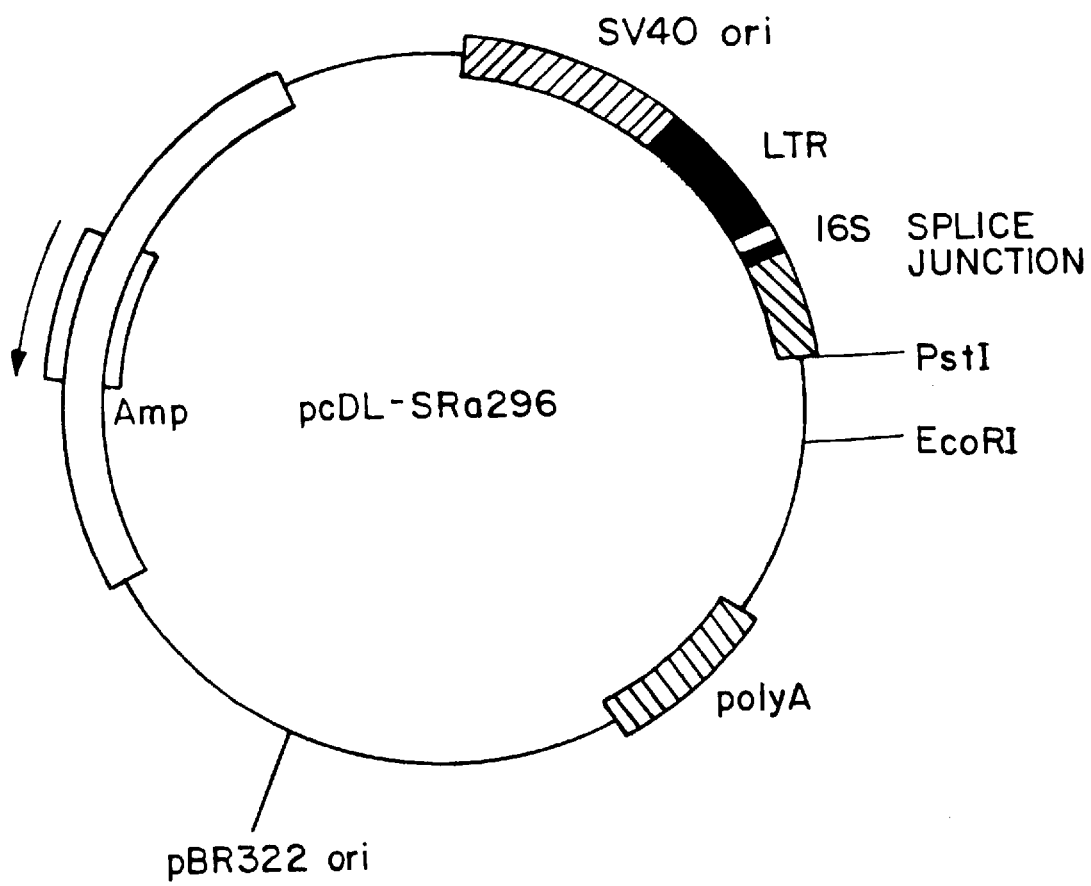
FIG. 1 depicts the structure of pcDL-SRα296.

The present invention provides a method for assaying exogenous protease activity in a host cell comprising the steps of:

(a) incubating a host cell transformed with a first nucleotide sequence encoding an exogenous protease and a second nucleotide sequence encoding an artificial polypeptide substrate under conditions which cause said exogenous protease and said artificial substrate to be expressed;

wherein said substrate comprises:

(i) a cleavage site for said exogenous protease; and (ii) a polypeptide that is secreted out of said cell following cleavage by said exogenous protease;

(b) separating said host cell from its growth media under non-lytic conditions; and (c) assaying said growth media for the presence of said secreted polypeptide.

As used herein, the term "exogenous protease" means a protease not normally expressed by the host cell used in the assay. That term includes full-length proteases that are identical to those found in nature, as well as catalytically active fragments thereof.

The choice of exogenous protease to be assayed is solely dependent upon the decision of the user. The only requirements are that: (1) the specificity of the enzyme in terms of what amino acid residues or sequences it cleaves at be known; (2) the primary structure of at least the catalytically active portion of the enzyme be known; and (3) a nucleotide sequence encoding at least an enzymatically active portion of the protease exists or can be made and can be expressed in a heterologous host cell.

According to a preferred embodiment, the exogenous protease is a protease encoded by a pathogenic agent. More preferred is a protease encoded by a pathogenic virus. Most preferably, the exogenous protease is the NS3 protease of hepatitis C virus ("HCV").

HCV NS3 protease is a 70 kilodalton protein that is involved in the maturation of viral polypeptides following infection. It is a serine protease which has a Cys-X or Thr-X substrate specificity. It has also been shown that the protease activity of NS3 resides exclusively in the N-terminal 180 amino acids of the enzyme. Therefore, nucleotide sequences encoding anywhere from the first 180 amino acids of NS3 up to the full length enzyme may be utilized in the methods of this invention. Active fragments of other known proteases may also be used as an alternative to the full-length protease.

According to an alternative embodiment, the invention provides a method for assaying endogenous protease activity in a host cell comprising the steps of:

a) incubating a host cell transformed with a nucleotide sequence encoding an artificial polypeptide substrate under conditions which cause said artificial substrate to be expressed;

wherein said substrate comprises:

i) a cleavage site for said endogenous protease; and ii) a polypeptide that is secreted out of said cell following cleavage by said endogenous protease;

b) separating said host cell from its growth media under non-lytic conditions; and c) assaying said growth media for the presence of said secreted polypeptide.

The term "endogenous protease", as used throughout this application, refers to a proteases that is normally expressed by the host cell. It includes both wild type proteases, as well as naturally occurring mutant proteases with increased or decreased activity.

According to the invention, the artificial polypeptide substrate used in the methods must comprise a cleavage site for the protease to be assayed; and must be secreted out of the cell following cleavage by that protease. Preferably, the DNA encoding the artificial substrate is derived from a gene or cDNA encoding a naturally occurring polypeptide that is normally cleaved and then secreted out of a cell, but not necessarily cleaved by the cell utilized in the assay.

The DNA encoding that polypeptide is then modified by inserting, in frame with the polypeptide coding sequence, nucleotides encoding a cleavage site that is recognized by the exogenous protease to be tested. If the cell utilized in the assay is capable of cleaving the substrate at its native cleavage site, then the nucleotides encoding the polypeptide's native cleavage site must be altered so as to render it uncleavable by endogenous proteases.

The protease cleavage site in the artificial substrate is preferably inserted within 60 amino acids on either side of the native cleavage site. Preferably, the artificial cleavage site is inserted N-terminal to the native cleavage site. Alternatively, the protease cleavage site can be created by mutating the native polypeptide sequence. Such mutation is preferably performed on a sequence within 60 amino acids, more preferably N-terminal to the native cleavage site and within 8–10 amino acids of the native cleavage site; or is a mutation of the native cleavage site itself.

Alteration of the native cleavage site to render it uncleavable by the host cell may be achieved, if necessary, by insertion, deletion or mutation of nucleotides at that site.

Insertion of the protease cleavage site into the substrate and alteration of its native cleavage site may be accomplished by any combination of a number of recombinant DNA techniques well known in the art, such as site directed mutagenesis or standard restriction digest/ligation cloning techniques. Alternatively, the DNA encoding all or part of the artificial substrate may be produced synthetically using a commercially available automated oligonucleotide synthesizer. Regardless of the techniques used to insert the protease cleavage site into the substrate polypeptide or alter its native cleavage site, it is crucial that the reading frame of the substrate polypeptide remain intact, without the insertion of stop codons.

The choice of secretable polypeptide from which the artificial substrate is derived may be selected from any pre-polypeptide that can be cleaved by and the resulting mature polypeptide secreted out of the host cell used for the assay, but is not normally present in that cell. For use in eukaryotic cells there are two main categories of pre-polypeptide from which the choice can be made.

The first and preferred category comprises pre-polypeptides that are expressed and cleaved in the cytoplasmic compartment. Among these proteins are interleukin-1β (IL-1β), interleukin-1a (IL-1α), basic fibroblast growth factor (bFGF) and endothelial-monocyte activating polypeptide II (EMAP-II). The advantage of using cytoplasmic pre-polypeptides is that there is a much greater likelihood that the protease and the artificial substrate will share the same subcellular compartment. This is because most proteases of interest are also cytoplasmic proteins and thus will have access to the artificial substrate.

The second category of pre-polypeptides that may be used to create artificial substrates used in the methods of this invention are those that are expressed on the cell surface through the organellar secretory pathway and are retained on the cell surface. Such substrates are useful to assay endogenous and exogenous cell membrane proteases, as well as exogenous proteases that are similarly engineered to be cell membrane proteins. The technique of creating a cell membrane protease or substrate involves cloning a leader peptide (i.e., signal sequence) onto the N-terminus of the substrate or protease and a hydrophobic, membrane anchor sequence (either a transmembrane domain or a glycosylphophatidylinositol anchor sequence) onto the C-terminus. The resulting substrate is a cell membrane protein with an extracellularly located cleavage site. When cleaved by a cell membrane protease on the same or a neighboring cell, the secreted polypeptide portion of the substrate is released into the media.

Examples of sequences that may be used for anchoring these proteins in the membrane are the transmembrane domains of TNFa precursor [Nedopsasov et al., *Cold Spring Harb. Symp. Quant. Biol.*, 51, pp. 611–24 (1986)], SP-C precursor [Keller et al., *Biochem J.*, 277, pp. 493–99 (1991) ], or alkaline phosphatase [Berger et al., *Proc. Natl. Acad. Sci. USA*, 86, pp. 1457–60 (1989)]. Techniques for cloning a signal sequence onto a cytoplasmic protein have been well documented [see, for example, Kizer and Trosha, *BBRC*, 174, pp. 586–92 (1991); Jost et al., *J. Biol. Chem.*, 269, pp. 26267–72 (1994) (expression and secretion of functional single chain Fv molecules using immunoglobulin light chain leader sequence); and Sasada et al., *Cell Structure Function*, 13, pp. 129–41 (1988)(secretion of human EGF and IgE in mammalian cells using an IL-2 leader sequence)], as have techniques for cloning a transmembrane anchor sequences onto cytoplasmic proteins [Berger et al., supra; Oda et al., *Biochem J.*, 301, pp. 577–83 (1984)]. By combining these two techniques, the protease or substrate of interest can be converted from a cytoplasmic protein into a cell surface membrane protein.

In order to insure that the substrate and protease will have access to one another and according to an alternate embodiment of the invention, the artificial substrate and an exogenous protease to be assayed may be encoded as part of a single polyprotein. That polyprotein may be a cytoplasmic or a membrane protein, as long as the substrate and protease domains reside in the same cellular compartment.

The choice of host cell to use in this method is virtually unlimited. Any cell that can grow in culture, be transformed or transfected with heterologous nucleotide sequences and can express those sequence may be employed in this method. These include bacteria, such as *E. coli*, Bacillus, yeast and other fungi, plant cells, insect cells, mammalian cells. In addition, expression of either of those sequences in higher eukaryotic host cells may be transient or stable. Preferably, the host cell is a higher eukaryotic cell that is incapable of cleaving the substrate at its native cleavage site. Preferably, the host cell is a mammalian cell. Most preferably, the host cell is a COS cell.

It will be apparent that the specific choice of cell is governed by the particular protease to be assayed and by the particular artificial substrate used. In embodiments that assay an exogenous protease, one obvious limitation is that the endogenous cellular enzymes of the chosen host must be unable to cleave the artificial substrate to any significant extent. The endogenous rate of artificial substrate cleavage may be determined by transforming the selected host cell with only the nucleotide sequence coding for the artificial substrate and then growing that host under conditions which cause expression of that nucleotide sequence and which would cause expression of the exogenous protease-encoding nucleotide sequence if that sequence were present. The growth media of the cell is then assayed for the presence of the secreted polypeptide portion of the substrate. In assays that measure exogenous protease activity, control cells (no exogenous protease expressed) should secrete less than 10% of the total amount of expressed substrate (due to endogenous cleavage and, in assays that do not distinguish between cleaved and uncleaved substrates, leeching of uncleaved substrate out of the cell) in order to be useful in the methods of this invention. When an endogenous protease is assayed, a controls for non-specific substrate cleavage is a cell transformed with a substrate that contain a mutation at the cleavage site. This mutation renders the substrate uncleavable by the specific endogenous protease being assayed, but still susceptible to non-specific cleavage. As with assays for exogenous proteases, control cells should secrete less than 10% of the total amount of expressed substrate.

In order to quantitate the protease activity, the amount of secreted substrate polypeptide is measured. Quantitation may be achieved by subjecting the growth media to any of the various standard assay procedures that are well known in the art. These include, but are not limited to, immunoblotting, ELISA, immunoprecipitation, RIA, other calorimetric assays, enzymatic assay or bioassay. Quantitation techniques that employ antibodies, preferably utilize antibodies that have low cross-reactivity with the uncleaved substrate. Preferably cross-reactivity is less than 20% and more preferably less than 5%.

According to another embodiment, the present invention provides a method of screening for protease inhibitors. In this method, the above-described assay is carried out in the presence and absence of potential inhibitors of the protease. When the assays of this invention are performed using cells which transiently express the substrate and protease, the inhibitor is preferably added immediately after transfection with the protease and substrate-encoding DNA sequences. When stable transformants are used, the potential inhibitor is added at the beginning of the assay. The efficacy of the potential inhibitor (and its ability to cross the cell membrane) is determined by comparing the amount of secreted substrate polypeptide present in the media of cells assayed in its presence versus its absence. Compounds which cause at least a 90% reduction in the amount of secreted substrate polypeptide are potentially useful protease inhibitors.

In order that the invention described herein may be more fully understood, the following examples are set forth. It should be understood that these examples are for illustrative purposes only and are not to be construed as limiting this invention in any manner.

EXAMPLE 1

Construction Of Expression Plasmids

A. HCV NS3 Protease

We cloned the nucleotide sequence coding for the entire, intact HCV NS3 protease, an NS3-4A polyprotein or a truncated NS3 consisting of amino acids 1 to 180 into the mammalian expression plasmid pcDL-SRα [Y. Takebe et al., *Mol. Cell. Biol.*, 8, pp. 466–72 (1988)]. That plasmid contains an SV40 origin of replication and an HTLV LTR enhancer/promoter sequence which ultimately drives the high level expression of the NS3 coding sequences (FIG. 1).

The respective NS-3 coding fragments (full length NS3, NS3-4A polyprotein or truncated NS3 (amino acids 1–181) were obtained by PCR of the corresponding portions of a full length HCV H strain cDNA (SEQ ID NO:1). For each of the three coding fragments the following 5' primer was used (SEQ ID NO:2): 5'GGACTAGTCTGCAGTCTAGAGCTCCATGGCGCCCATCACGGCGTACG3'. The fragment-specific 3' primers used were:
NS3—(SEQ ID NO:3):
3'GAAGATCTGAATTCTAGATTTTACGTGACGACCTCCACGTCGGC5';
NS3-4A—(SEQ ID NO:4):
3'GAAGATCTGAATTCTAGATTTTAGCACTCTTCCATCTCATCGAA5'; and
NS3(1–181)—(SEQ ID NO:5):
3'GAAGATCTGAATTCTAGATTTTAGGATCTCATGGTTGTCTCTAGG5'. These primers produced PCR-amplified fragments containing multiple restriction sites at either end for ease of cloning.

In order to ligate the fragments to the vector, the vector was first cleaved with PstI and EcoRI to remove a small fragment. The cut vector was then purified and ligated to the respective PstI/EcoRI cut NS3 protease-encoding fragment.

B. IL-1β/NS3 Substrate

A derivative of plasmid pKV containing the pre-IL-1β coding sequence has been described by P. K. Wilson et al., *Nature*, 370, pp. 253–70 (1994). That plasmid contains the SV40 origin of replication and the early promoter. The pre-IL-1β sequence was cloned between the SpeI and BglII sites shown in FIG. 2.

We inserted a double stranded synthetic DNA fragment (SEQ ID NO:6) which encoded 20 amino acids: SEQ ID NO:7: GADTEDVVCCSMSYTWTGVH and contained linkers at both ends that included an ApaL1 restriction site. The DNA was cloned into the ApaL1 site in pre-IL-1β (between the codons for amino acids $His_{115}$ and $Asp_{116}$), immediately upstream of the native cleavage site (located between $Asp_{116}$ and $Ala_{117}$). The first 18 amino acids of the insert correspond to the HCV peptide 5A/5B cleavage site. The last two amino acids are encoded by the linker. The inserted DNA maintained the reading frame of the native pre-IL-1β protein. The resulting substrate is referred to throughout the application as "pre-IL-1βB*".

NS3 cleaves the inserted peptide in between the cysteine and serine residues. Because the COS cells we utilized in this assay were incapable of cleaving pre-IL-1β (data not shown), we did not have to knock out the native pre-IL-1β cleavage site.

In another construct, we performed site directed mutagenesis to alter the native pre-IL-1β cleavage site of $Asp_{116}$-$Ala_{117}$-$Pro_{118}$ to Cys-Ser-Met, a conserved recognition sequence for NS3. This construct is referred to throughout the application as "pre-IL-1βB (CSM)".

C. NS3-4A-Δ4B-IL-1β

In order to create a single fusion polypeptide that encoded both the exogenous protease and the polypeptide substrate, we utilized the fact that NS3 can autoprocess (cleave) an NS3-4A–4B polyprotein at both the NS3-4a and 4A–4B junctions.

We isolated a DNA fragment that encoded NS3-4A and the first 60 amino acids of 4B through PCR using the HCV strain H cDNA referred to above (SEQ ID NO:1) and the following primers: SEQ ID NO:8:
5'GGACTAGTCTGCAGTCTAGAGCTCCATGGCGCCCATCACGGCGTACG3' and SEQ ID NO:9:
3'GGACGCGGTCTGCAGGAGGCCGAGGGC5'. The PCR products were digested with PstI and XbaI prior to cloning.

The mature IL-1B portion of the construct (amino acids 117–269 of SEQ ID NO:11) was created by PCR cloning of full length pre-IL-1β cDNA (SEQ ID NO:10) using the following primers:
SEQ ID NO:12: 5'CTCGGCCTCCTGCAGGCACCTGTACGATCACTGAAC3 '; and SEQ ID NO:13:
3'GGGAATTCTAGATTTTAGGAAGACACAAATTG5'. These PCR products were digested with PstI and EcoRI prior to cloning.

The NS3-4A-Δ4B and IL-1β fragments were then ligated together with XbaI/EcoRI digested pcDL-SRα to obtain the desired construct.

As a control we created a mutant NS3 protease fusion protein construct. This construct was identical to the one described above, except that the NS3 portion was created by PCR using the same primers and the cDNA of the NS3 active site mutant S1165A [A. Grakoui et al., *J. Virol.*, 67, pp. 2832–43 (1993)]. The NS3 active site mutant contains a serine-to-alanine mutation in its active site, rendering the enzyme inactive.

EXAMPLE 2

Transfection Of COS Cells And Assay Of Secreted IL-1β

The expression plasmid constructs described in Example 1 were transfected into COS-7 cells using the DEAE- Dextran transfection protocol [Gu et al., Neuron, 5, pp. 147–57 (1990)]. COS cells in 6-well clusters or 100 mm dishes at 50% confluency were transfected with 4–10 μg of the desired plasmid in a DEAE-Dextran solution. Following transfection, the cells were incubated an additional 48 hours before assaying.

The processing of pre-IL-1β or NS3-4A-Δ4B-IL-1β fusion protein and subsequent secretion of mature IL-1β into the media was measured by ELISA of IL-1β using an antibody that was specific for mature IL-1β (approx. 3% cross-reactivity with pre-IL-1β). We analyzed expression by harvesting the COS cells in ice-cold phosphate buffered saline, lysing the cells in a 0.1% Triton X-100 buffer and centrifuging the lysate to remove cell debris. The lysates were then analyzed by SDS-PAGE and immunoblotting using an IL-1β antibody (Genzyme) and an NS3 antibody. Alternatively, expression, processing and secretion was analyzed by labelling the cells for 24 hours in the presence of [$^{35}$S]-methionine, incubating the cells for an additional 24 hours after the label was removed and then utilizing immunoprecipitation and SDS-PAGE to analyze the polypeptides.

EXAMPLE 3

Figure 3A:
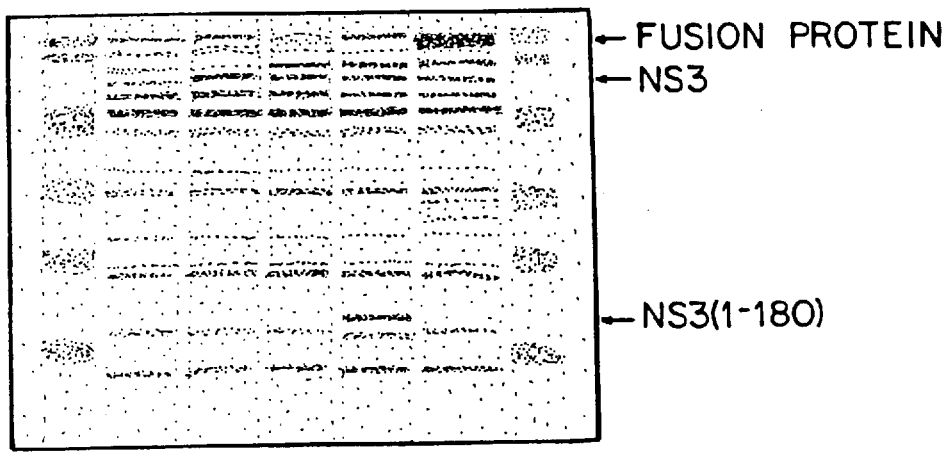
FIG. 3, panel A, is an immunoblot of cell lysates from cells transfected with a NS3-wild-type or NS3-mutant NS3-4A-4B-IL1β or cotransfected with a NS3-mutant NS3-4A-4B-IL1β and a NS3(1-180) construct probed with an anti-NS3 antibody.
Figure 3B:
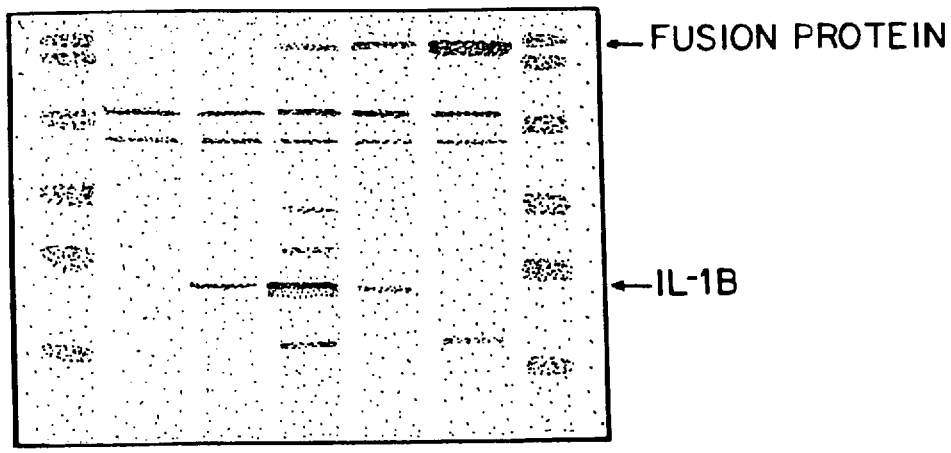

NS3-Specific Processing Of An NS3-4A-Δ4B-IL-1β Fusion Protein And Secretion Of Δ4B-IL-1β Into The Media Transfectants expressing the NS3-4A-Δ4B-IL-1β fusion protein autoprocessed that protein at both the NS3-4A and 4A-4B junctions. The cell lysates of these transfectants were subjected to Western blotting utilizing an anti-NS3 antibody. FIG. 3, panel A, Wt-1 and Wt-2 lanes, shows that this experiment produced a doublet band in the 70 kD area, present only as a single band in the untransformed control cells (panel A, No DNA lane). The second band of the doublet in the Wt-1 and Wt-2 lanes corresponds to the size of mature NS3. A transfectant that expressed an inactive mutant NS3-containing NS3-4A-Δ4B-IL-1β fusion protein demonstrated no 70 kDa doublet and therefore was not autoprocessed (NS3 mutant lane). A transfectant that co-expressed the same mutant fusion protein together with a truncated, but active NS3—NS3(1–180)—was also analyzed. Surprisingly, the mutant fusion protein did not appear to be cleaved by NS3(1-180), as indicated by the lack of a doublet in the 70 kDa region (NS3 mutant+NS3(1–180) lane). However, a 20 kDa band representing the truncated NS3 was detected in that lysate, as indicated by the NS3 (1–180)arrow.

A similar experiment performed on cell lysates utilizing an mature IL-1β-specific antibody demonstrated the presence of a band corresponding in size to the Δ4B-IL-1β portion of the fusion protein in both the NS3-4A-Δ4B-IL-1β transfectants (FIG. 3, panel B, Wt-1 and Wt-2 lanes) and, to a lesser degree in the NS3 mutant fusion protein/NS3 (1–180) cotransfectant. Virtually no IL-1β was detected in the NS3 mutant fusion protein expressing transfectant (IL-1β arrow). These experiments confirm that the cleavage observed in the wild type NS3-4A-Δ4B-IL-1β transfectants was dependent upon NS3 protease activity. Thus, we had proof that cleavage of this fusion protein was essentially NS3-dependent and not caused by some endogenous protease.

Figure 4:
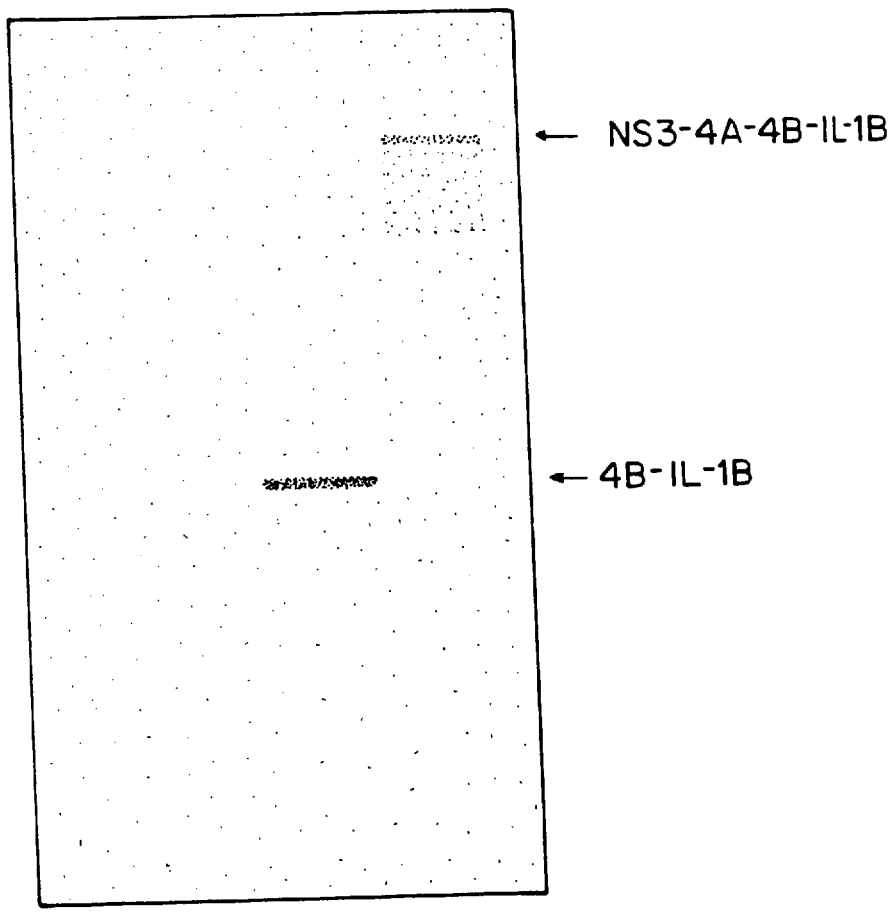
FIG. 4 depicts the immunoprecipitation of the media from $^{35}$S-labelled cells transfected with either a NS3-wild-type or NS3-mutant NS3-4A-4B-IL1β construct with an anti-IL-1β antibody.

Secretion of the cleaved substrate was determined by assaying culture media with a commercially available mature IL-1β-specific ELISA assay (R&D Systems, Minneapolis, Minn.). For the wild-type NS3-containing construct we detected a concentration of 2.5 μg/ml of IL-1β in the medium. We detected less than 0.25 μg/ml of IL-1β in the media of cells transfected with the mutant NS3-containing construct. Immunoprecipitation experiment utilizing the same anti-IL-1β antibody demonstrated the presence of Δ4B-IL-1β in the media of cells containing the wild type NS3-containing construct, but none from the mutant NS3-containing construct (FIG. 4), thus confirming these results.

EXAMPLE 4

NS3-Specific Processing Of Mutated Pre-IL-1β Containing An Artificial Cleavage Site And Secretion Of IL-1β Into The Media We confirmed that NS3 protease can cleave artificial substrates other than an HCV polypeptide by cotransfecting COS cells with the NS3-4A and either of the pre-IL-1β-containing artificial substrate expression constructs described in Example 1C.

Figure 5:
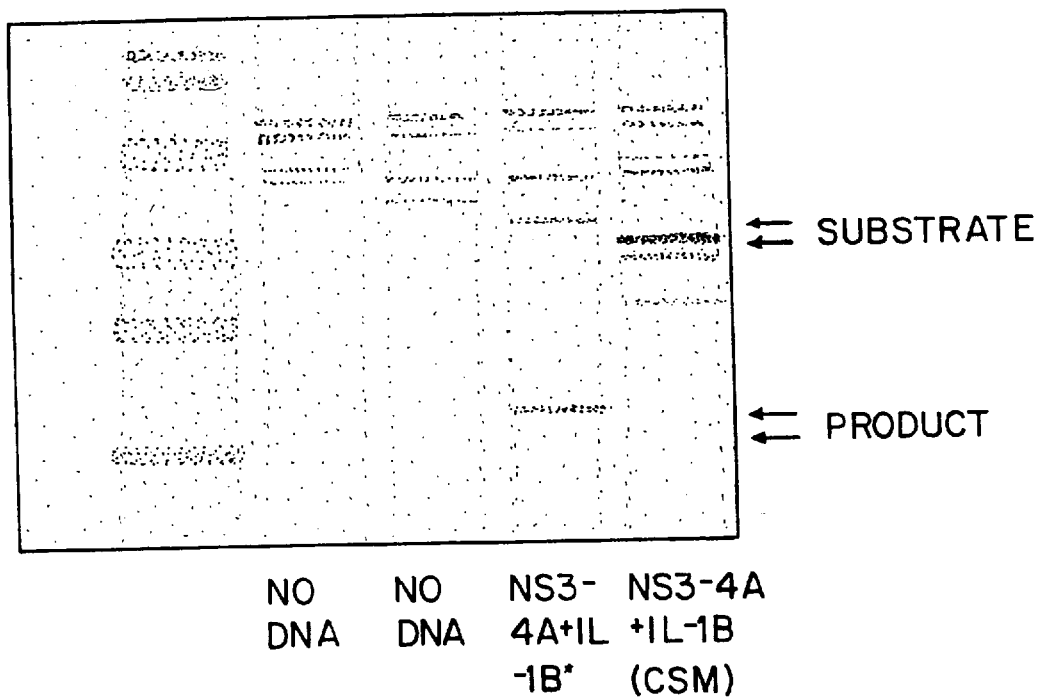
FIG. 5 is an immunoblot of cell lysates from cells co-transfected with NS3-4A and either a NS5A/5B- or CSM-containing pre-IL1β substrate probed with an anti-IL-1β antibody.
Figure 6:
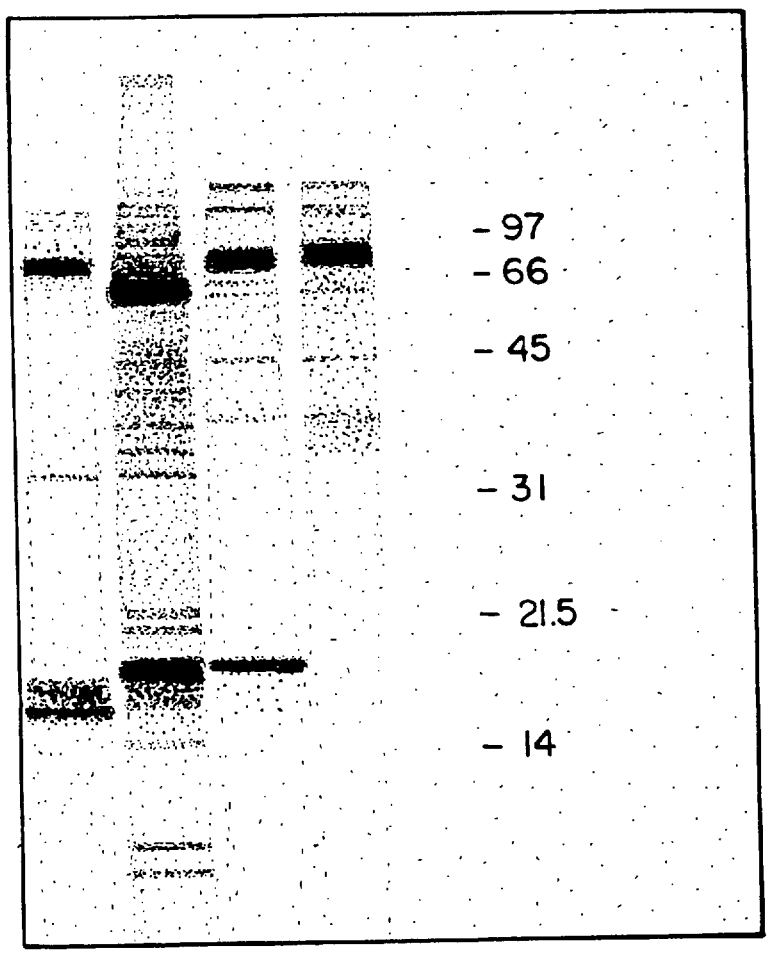
FIG. 6 depicts the immunoprecipitation of the media from $^{35}$S-labelled cells co-transfected with NS3-4A and either a NS5A/5B- or CSM-containing pre-IL1β substrate with an anti-IL-1β antibody.

Co-expression of the NS3-4A and pre-IL-1β* substrate sequences resulted in rapid cleavage of the substrate and concomitant secretion of a 19 Kd IL-1β into the media. Secretion was quantitated using an ELISA specific for the processed form of IL-1β. An immunoblot of cell lysates from these transformants demonstrated the presence of both cleaved and uncleaved substrate (FIG. 5, NS3-4A+IL-1β* lane). The same experiment was performed using cells that were metabolically labelled with [$^{35}$S]-methionine, followed by immunoprecipitation of the media with the processed IL-1β-specific antibody. The results of the immunoprecipitation experiment are shown in FIG. 6, NS3-4A+pre-IL-1β* lanes.

When we coexpressed NS3-4A and the pre-IL-1β (CSM) sequences, we also observed cleavage of the substrate at the predicted Cys$_{116}$-Ser$_{117}$ site. Both cleaved and uncleaved forms were observed in cell lysates using immunoblotting specific for IL-1β (FIG. 5, NS3-4A+IL-1β (CSM) lane). Immunoprecipitation of the media from [$^{35}$S]-methionine labelled cells also demonstrated the presence IL-1β-containing cleavage product, but less than that observed for the 5A-5B-containing pre-IL-1β substrate (FIG. 6, NS3-4A+pre-IL-1β (CSM) lane).

EXAMPLE 5

Assay of NS3 Inhibitors

We tested the potential of compounds VH-15924 and VH-16075 as HCV NS3 protease inhibitors in our assays.

Transfectants expressing the NS3-4A-Δ4B-IL-1β were grown in the presence of varying amounts VH-15924. Even at concentrations as high as 100 μM, we detected the presence of the cleavage product, Δ4B-IL-1β, in the media. This indicated that VH-15924 was not an effective inhibitor of NS3 protease.

We also assayed the inhibition of cleavage and secretion of pre-IL-1β* substrate by both VH-15924 and VH-16075.

Figure 7:
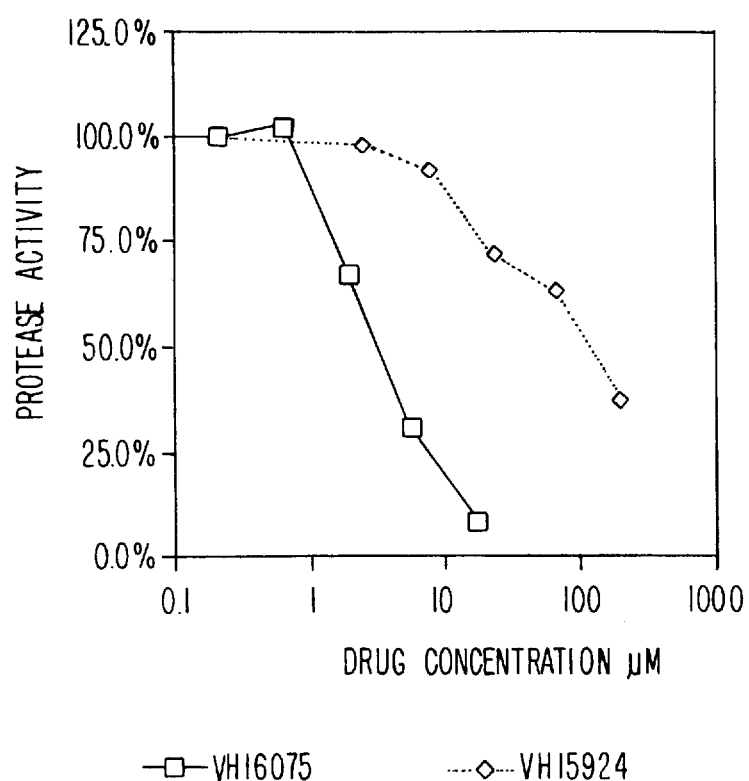
FIG. 7 depicts the inhibition of HCV NS3 protease cleavage of pre-IL-1β* by varying concentrations of VH16075 and VH15924.

VH-16075 inhibited cleavage and secretion with an IC$_{50}$ of 4 µM. As in the previous experiment, VH-15924 did not completely inhibit cleavage/secretion even at concentrations of 100 µM (FIG. 7).

While I have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

I claim:

1. A method for assaying Hepatitis C virus protease activity in a eukaryotic host cell comprising the steps of:
    a. incubating a host cell transformed with a first nucleotide sequence encoding a Hepatitis C virus protease and a second nucleotide sequence encoding a non-native polypeptide substrate that is cleaved in the cytoplasmic compartment;
    wherein said substrate comprises:
        i. a cleavage site for said Hepatitis C virus protease;
        ii. a polypeptide portion that is secreted out of said cell following cleavage by said Hepatitis C virus protease; and
        iii. a polypeptide portion that remains in said cell following cleavage by said Hepatitis C virus protease;
    under conditions which cause said Hepatitis C virus protease and said substrate to be expressed, wherein less than 10% of said substrate is secreted out of the host cell prior to cleavage and wherein said protease is not secreted out of the host cell;
    b. separating said host cell from its growth media under non-lytic conditions; and
    c. assaying said growth media for the presence of said secreted polypeptide.

2. A method for identifying a compound as an inhibitor of a protease comprising the steps of:
    (a) assaying the activity of a protease in the absence of said compound by a method according to claim 1;
    (b) assaying the activity of a protease in the presence of said compound by a method according to claim 1, wherein said compound is added to the host cells during said incubation of said host cells; and
    (c) comparing the results of step (a) with the results of step (b).

3. The method according to claim 1 or claim 2, wherein said first nucleotide sequence and said second nucleotide sequence encode a single polypeptide.

4. The method according to claim 3, wherein said first and second nucleotide sequences encode NS3-4A-Δ4B-IL-1β (nucleotides 3419–5561 of SEQ ID NO:1 inserted upstream of nucleotides 435–893 of SEQ ID NO:10).

5. The method according to claim 1 or claim 2, wherein said first nucleotide sequence encodes a Hepatitis C virus protease or an enzymatically active fragment thereof.

6. The method according to claim 5, wherein said first nucleotide sequence encodes hepatitis C virus NS3 protease (nucleotides 3419–5312 of SEQ ID NO:1), an NS3-4A fusion protein (nucleotides 3419–5474 of SEQ ID NO:1) or amino acids 1–180 of NS3 protease (encoded by nucleotides 3419–3959 of SEQ ID NO:1).

7. The method according to claims 1 or 2, wherein said secreted polypeptide is selected from polypeptides comprising mature interleukin-1β (IL-1β), mature interleukin-1α (IL-1α), basic fibroblast growth factor and endothelial-monocyte activating polypeptide II.

8. The method according to claim 7, wherein said secreted polypeptide comprises mature IL-1β.

9. The method according to claim 8, wherein said artificial polypeptide substrate is selected from pre-IL-1β* (SEQ ID NO:7 inserted between His$_{115}$ and Asp$_{116}$ SEQ ID NO: 11) or pre IL-1β (CSM) (SEQ ID NO: 10).

10. A eukaryotic host cell transformed with a nucleotide sequence encoding a non-native polypeptide substrate that is cleaved in the cytoplasmic compartment, wherein said substrate comprises:
   a. a cleavage site for a Hepatitis C virus protease;
   b. a polypeptide portion that is secreted out of said cell following cleavage by said Hepatitis C virus protease; and
   c. a polypeptide portion that remains in said cell following cleavage by said Hepatitis C virus protease;
said host cell being capable of expressing said Hepatitis C virus protease and said substrate, wherein less than 10% of said substrate is secreted out of the host cell prior to cleavage and wherein said Hepatitis C virus protease is not secreted out of said host cell.

11. A eukaryotic host cell transformed with a first nucleotide sequence encoding a Hepatitis C virus protease and a second nucleotide sequence encoding a non-native polypeptide substrate that is cleaved in the cytoplasmic compartment, wherein said substrate comprises:
   a. a cleavage site for said Hepatitis C virus protease;
   b. a polypeptide portion that is secreted out of said cell following cleavage by said Hepatitis C virus protease; and
   c. a polypeptide portion that remains in said cell following cleavage by said Hepatitis C virus protease;
said host cell being capable of expressing said protease and said substrates wherein less than 10% of said substrate is secreted out of the host cell prior to cleavage and wherein said protease is not secreted out of said host cell.

12. The host cell according to claim 10 or 11, wherein said secreted polypeptide is selected from polypeptides comprising mature IL-1β, mature IL-1α, basic fibroblast growth factor and endothelial-monocyte activating polypeptide II.

13. The host cell according to claim 12, wherein said secreted polypeptide comprises mature IL-1β.

14. The host cell according to claim 13, wherein said artificial polypeptide substrate is selected from pre-IL-1β* (SEQ ID NO:7 inserted between His$_{115}$ and Asp116 of SEQ ID NO: 11) or pre-IL-1β (CSM) (SEQ ID NO: 10).

15. The host cell according to claim 11, wherein said first nucleotide sequence and said second nucleotide sequence encode a single polypeptide.

16. The host cell according to claim 15, wherein said first and second nucleotide sequences encode NS3-4A-Δ4B-IL-1β (nucleotides 3419–5552 of SEQ ID NO:1 inserted upstream of nucleotides 435–897 of SEQ ID NO:10).

17. The host cell according to claim 11, wherein said first nucleotide sequence encodes a Hepatitis C virus protease or an enzymatically active fragment thereof.

18. The host cell according to claim 17, wherein said first nucleotide sequence encodes hepatitis C virus NS3 protease (nucleotides 3419–5312 of SEQ ID NO:1), an NS3-4A fusion protein (nucleotides 3419–5474 of SEQ ID NO:1) or amino acids 1–180 of NS3 protease (encoded by nucleotides 3419–3959 of SEQ ID NO:1).

19. The host cell according to claim 10 or 11, selected from a group consisting of fungi including yeast, plant cells, insect cells, and mammalian cells.

20. The host cell according to claim 19, wherein said host cell is a mammalian cell.

21. The host cell according to claim 20, wherein said host cell is a COS cell.

* * * * *

UNITED STATES PATENT AND TRADEMARK OFFICE
CERTIFICATE OF CORRECTION

PATENT NO. : 5,861,267
DATED : January 19, 1999
INVENTOR(S) : Michael Su

It is certified that error appears in the above-identified patent and that said Letters Patent is hereby corrected as shown below:

Column 1, line 48 change "cotransfroming" to
-- cotransforming --.

Column 2, line 10 change "the a" to -- the α --.

Column 4, line 46 change "proteases" to -- protease --.

Column 5, line 35 change "interleukin-1a" to
-- interleukin-1α --.

Column 6, line 25 change "sequences" to -- sequence --.

Column 6, line 56 change "controls" to -- control --.

Column 6, line 57 change "contain" to -- contains --.

Column 8, line 3 change "BgIII" to -- BglII --.

Column 8, line 41 change "IL-1B" to -- IL-1β --.

Column 9, line 40 change "-A4B-" to -- -4B- --.

Column 10, line 10 change "A4B-" to -- Δ4B- --.

Signed and Sealed this

Twenty-sixth Day of December, 2000

Attest:

Q. TODD DICKINSON

Attesting Officer

Director of Patents and Trademarks